US00PP09692P

United States Patent [19]

van Rijn

[11] Patent Number: Plant 9,692

[45] Date of Patent: Nov. 12, 1996

[54] CALATHEA PLANT NAMED 'ANGELA'

[75] Inventor: Magdalena J. M. van Rijn, Schipluiden, Netherlands

[73] Assignee: Van Rijn Plants, Am Schipluiden, Netherlands

[21] Appl. No.: 510,300

[22] Filed: Aug. 2, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A Calathea plant named 'Angela' having oval leaves with a dark-green center and a pink-purple margin on young leaves. The mature leaves have a green center with dark green strips parallel to the primary veins that are bordered first by a bright silver-green margin and then by a dark green margin. The lower side of the leaves is dull purple-red.

7 Drawing Sheets

The present invention comprises a new and distinct cultivar of Calathea, botanically known as *Calathea roseo* picta, and referred to by the cultivar name 'Angela.'

The new cultivar is a random mutation and was discovered and selected from a group of *C. roseo* picta plants in March 1989 in Schipluiden, The Netherlands, by the inventor Magdalena J. M. van Rijn.

Propagation by tissue culture at the above noted location increased the number of plants for evaluation and has demonstrated the stability of the combination of characteristics of 'Angela' from generation to generation.

The following observations, measurements and values were taken at 's-Gravenzande, The Netherlands and describes plants grown in the Nursery Schipluiden under greenhouse conditions which closely approximating those generally used in horticultural practice.

The following traits have been repeatedly observed to be characteristics which in combination distinguish 'Angela' from others of the same species.

1. The plant produces leaves with a purple mid-rib. Parallel to the primary veins are dark green strips on a light green center and both are bordered by a green colored margin. This margin has a purple blush which gets darker towards the base of the leaf. The margin on the upper leaf surface is dotted dark green and the outermost margin is purple.

2. The leaf margin of young leaves is purple-red which becomes dark green as the leaf matures.

3. The lower side of the leaf is dull purple-red.

4. The leaf stalk from the leaf base to the geniculum is purple-red.

All color references are to The Royal Horticultural Society Colour Chart (R.H.S.). The color values were determined between 11:30 h and 12:00 h on Apr. 7, 1995 under natural light with a light intensity of 1210 J/m$^2$ at 's-Gravenzande, The Netherlands.

Phenotypic characteristics may vary somewhat depending on horticultural practices such as light level and fertilization rate, among others, without, however, any variance in genotype.

The accompanying color photographic drawings show an 'Angela' that is 9.5 months old grown in a 19 cm pot.

Sheet 1 is a top perspective of the plant.

Sheet 2 and 3 are a top/side and side perspective of 'Angela', respectively.

Sheet 4 shows the upper surface of a young leaf of the plant.

Sheets 5 and 6 show the upper surface of young to mature leaves of 'Angela.'

Finally, sheet 7 shows the upper surface of a mature leaf of 'Angela.'

Origin: Mutation of *Calathea roseo* picta.

Classification: *Calathea roseo* picta, cv. 'Angela'.

Propagation: Asexual production either by tissue culture or division.

Plant: Age: 9.5 months Pot size: 19 cm.

*Height.*—35–42 cm.

*Width.*—52–66 cm.

*Branching.*—Good.

*Growth habit.*—Compact.

Leaves:

*Form.—Ovate, mucronulate tip, entire margins.*

*Size.*—Mature about 25 cm long×15 cm wide.

*Petiole.*—Size: Approximately 17 cm–25 cm. Color: R.H.S. 187 A (purple-red).

*Petiole winds.*—Size: Approximately 9 cm long and 8 mm wide. Color: R.H.S. 187 C, (purple-red).

*Geniculum.*—Size: 30–40 mm long and 4–6 mm wide. Color: R.H.S. 177 A.

*Veins.*—Shape: Midrib sunken, leaf blade slightly concave between veins. Midrib protrudes from the lower surface. Color: Midrib from the base purple-red becoming brighter in color toward the leaf tip. Primary veins are dark green.

*Color.—Upper surface: Young: Margin: outermost margin R.H.S.* 139 A (green-black); innermost margin R.H.S. 66 C (shiny pink-purple). Leaf center: R.H.S. 139 A with darker green-black dark green stains of R.H.S. 137 A. Mature: Margin: outermost margin R.H.S. 137 A (dark green) margin R.H.S. 193 A (bright silver-green). Leaf center: R.H.S. 138 C–D (bright green). Primary veins: R.H.S. 139 A or darker with strips 2 cm wide. Midrib: R.H.S. 59 C, brown red. Lower surface: R.H.S. 187 A (dull purple red). Midrib: R.H.S. 177 A (brown red). Margin: R.H.S. 187 A (dull purple-red).

Roots: Thin white roots.

General oservations: Calathea 'Angela' has oval leaves with a dark-green center and a pink-purple margin on young leaves. The mature leaves have a green center with dark green strips parallel to the primary veins that are bordered first by a bright silver-green margin and then by a dark green margin. The lower side of the leaves is dull purple-red.

| CLOSEST COMPARISON CULTIVAR | | |
|---|---|---|
| Characteristic | Cultivar 'Silvia' | Cultivar 'Angela' |
| Leaf center (young) | RHS 59C, stains of RHS 191B | RHS 139A, stains of RHS 137A |
| Leaf center (mature) | RHS 139D, splashes RHS 59C | RHS 138C, strips of RHS 139A |
| Margin mature leaf | RHS 136A, dark green | RHS 193A, bright green |

-continued

| CLOSEST COMPARISON CULTIVAR | | |
|---|---|---|
| Characteristic | Cultivar 'Silvia' | Cultivar 'Angela' |
| Plant height | 45 cm–51 cm | 35 cm–42 am |
| Plant width | 46 cm–56 cm | 52 cm–66 cm |

I claim:

1. A new and distinct cultivar of Calathea plant named 'Angela,' as illustrated and described.

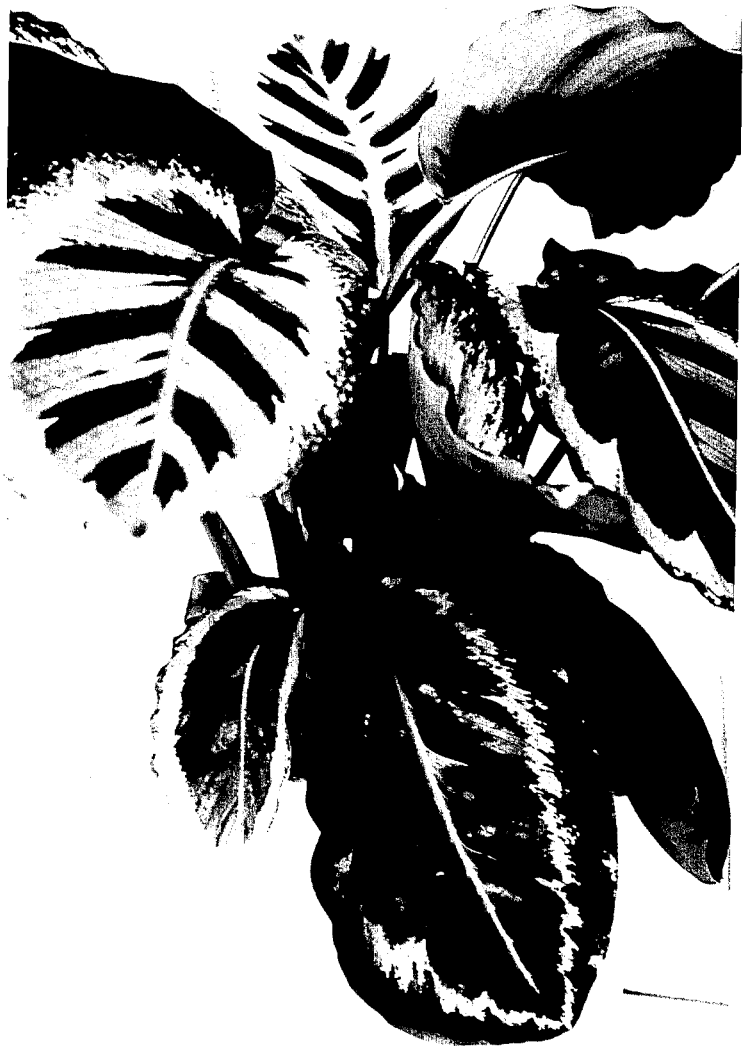

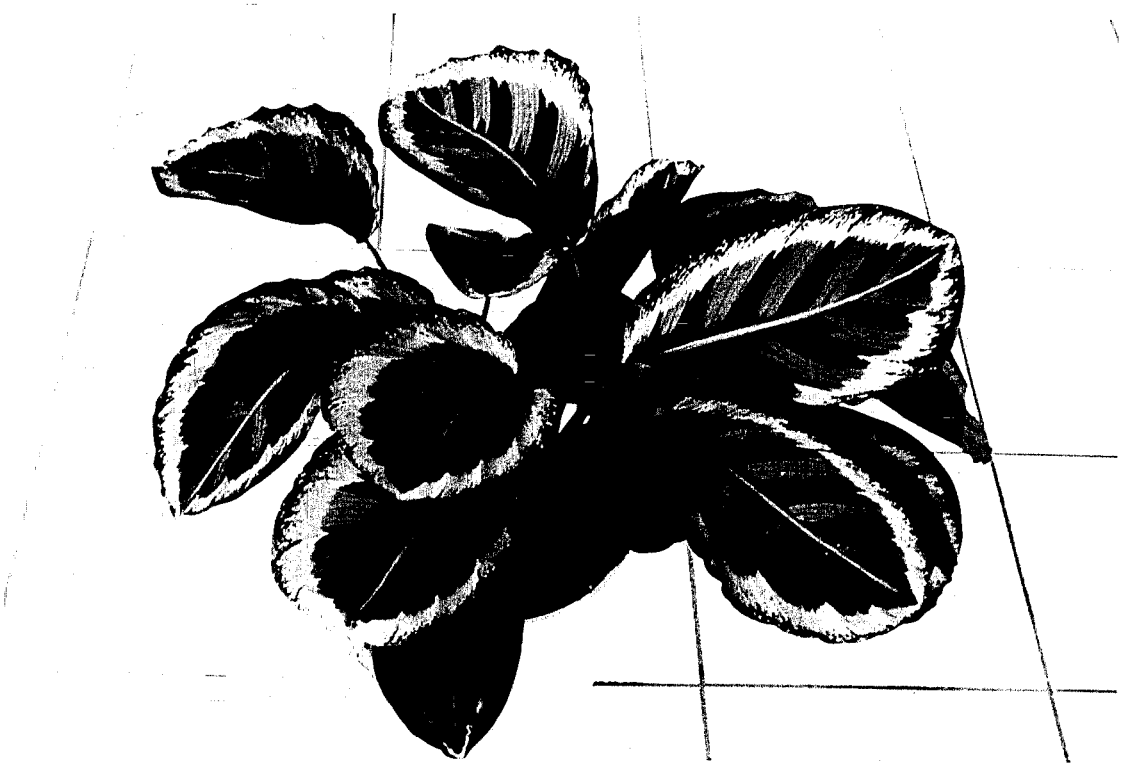

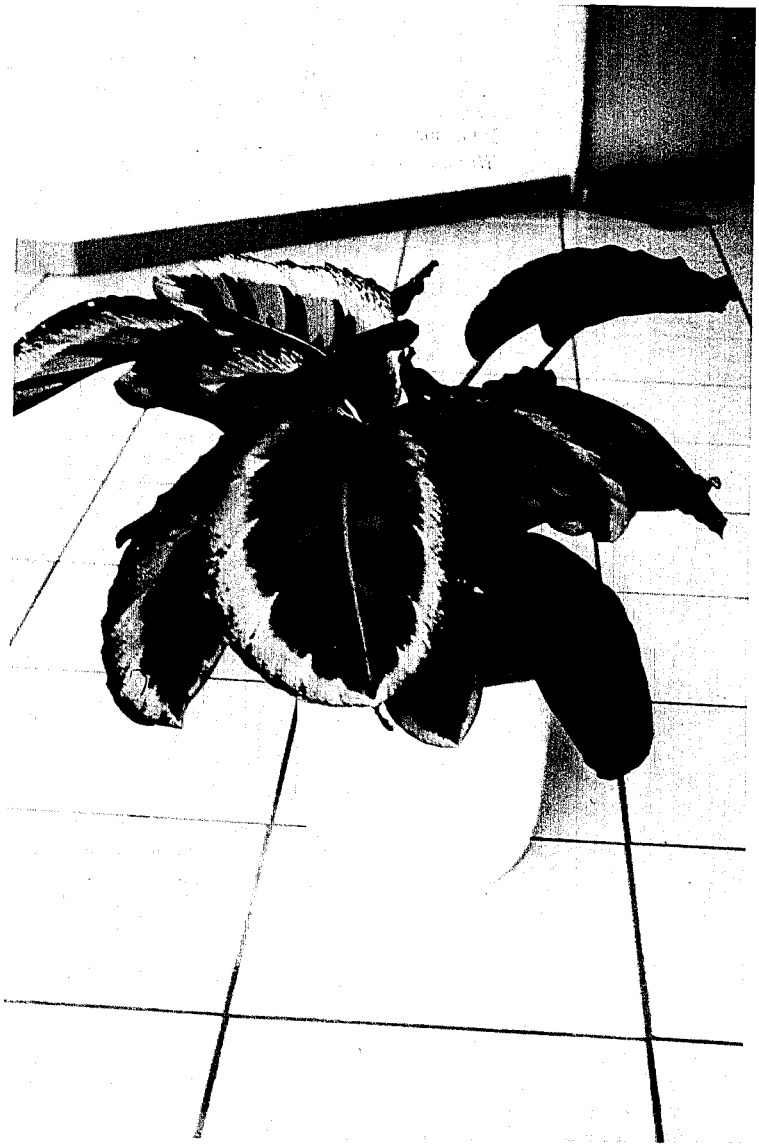

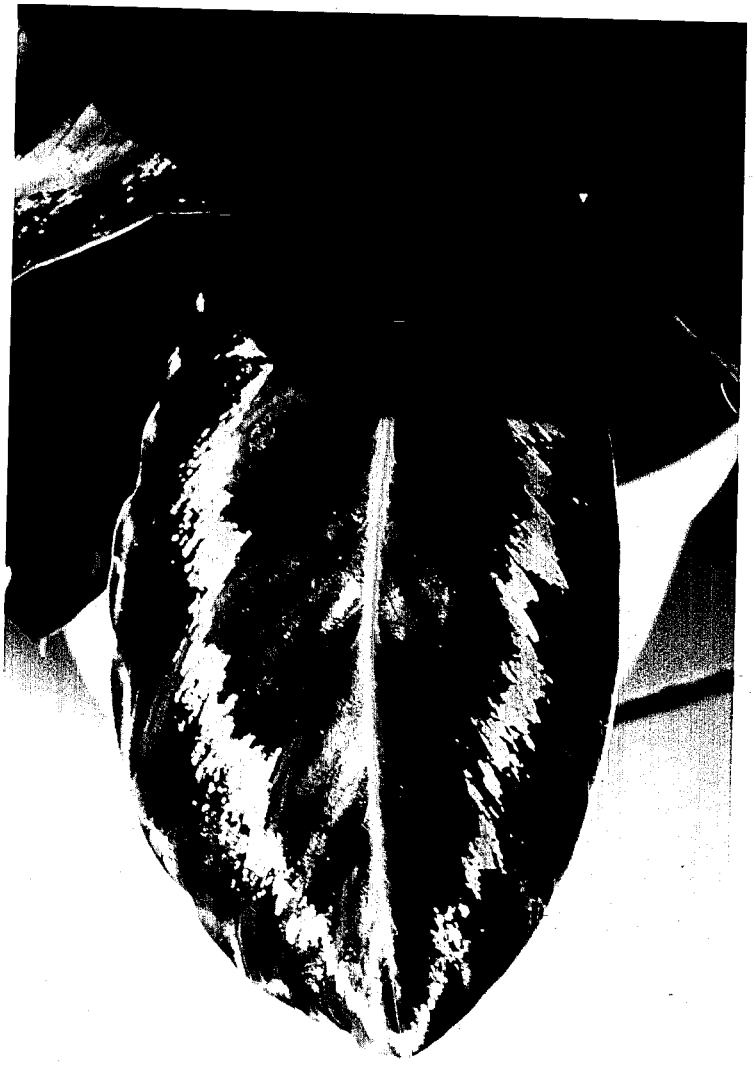

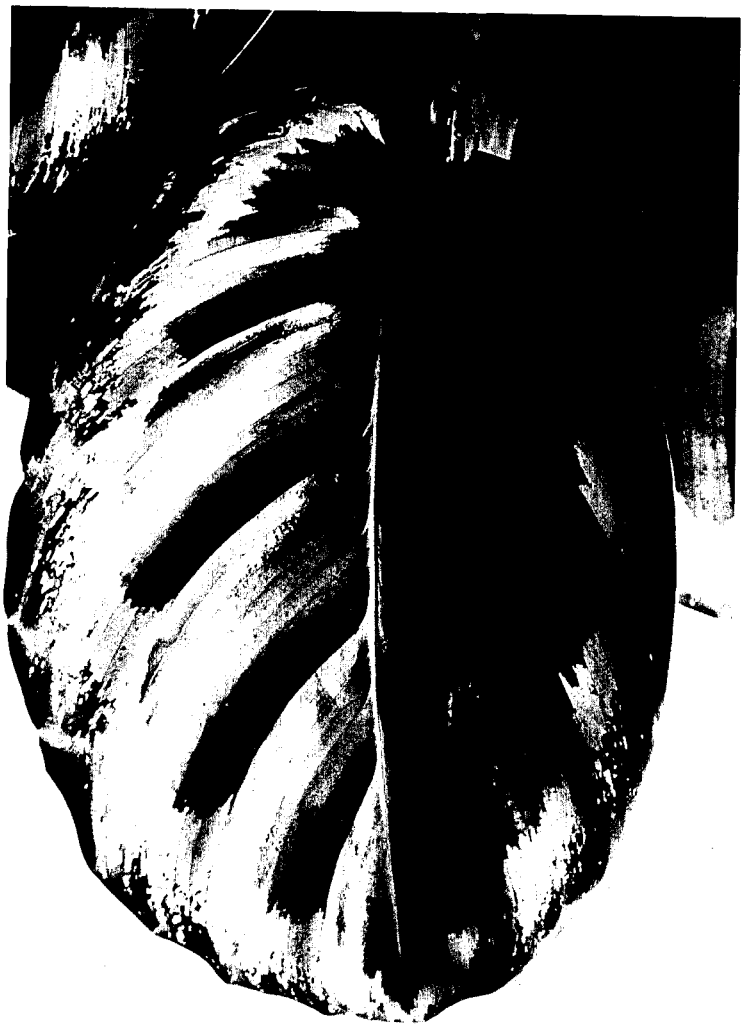

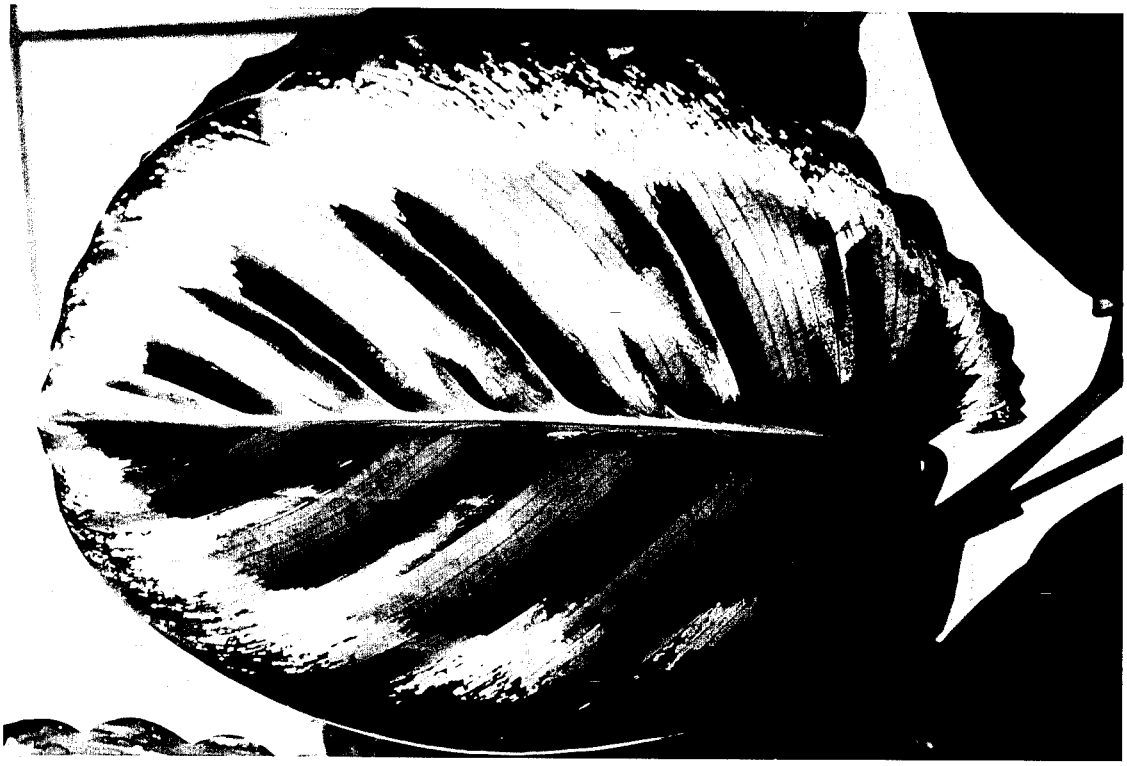

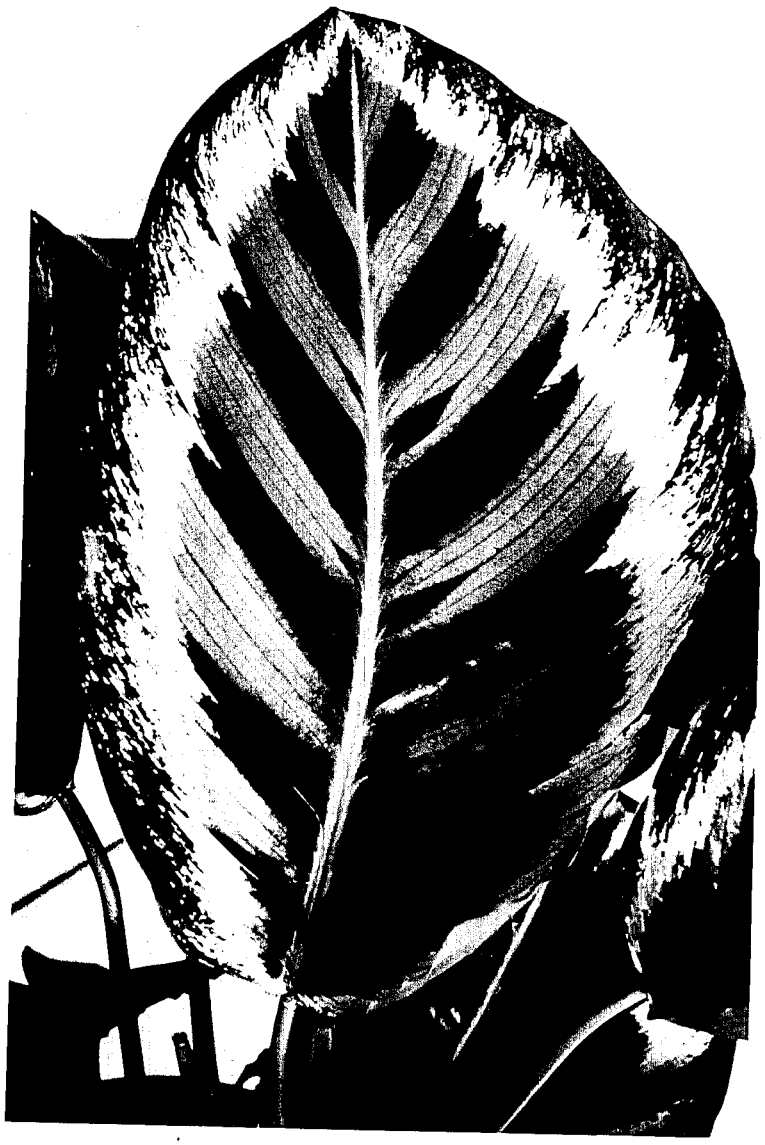

* * * * *